US012465474B2

(12) United States Patent

Yeniel

(10) Patent No.: US 12,465,474 B2
(45) Date of Patent: *Nov. 11, 2025

(54) READJUSTABLE MIDURETHRAL SLING

(71) Applicant: SORANUS ARGE VE DANISMANLIK HIZMETLERI SANAYI TICARET A.S., Izmir (TR)

(72) Inventor: Ahmet Ozgur Yeniel, Izmir (TR)

(73) Assignee: SORANUS ARGE VE DANISMANLIK HIZMETLERI SANAYI TICARET A.S., Izmir (TR)

(*) Notice: Subject to any disclaimer, the term of this patent is extended or adjusted under 35 U.S.C. 154(b) by 0 days.

This patent is subject to a terminal disclaimer.

(21) Appl. No.: 18/583,918

(22) Filed: Feb. 22, 2024

(65) Prior Publication Data

US 2024/0216117 A1 Jul. 4, 2024

Related U.S. Application Data

(63) Continuation of application No. 17/276,497, filed as application No. PCT/TR2019/050940 on Nov. 12, 2019, now Pat. No. 11,944,527.

(30) Foreign Application Priority Data

Nov. 13, 2018 (TR) ................................ 2018/17068
Jul. 31, 2019 (TR) ................................ 2018/11551

(51) Int. Cl.
*A61F 2/00* (2006.01)

(52) U.S. Cl.
CPC .... *A61F 2/0045* (2013.01); *A61F 2220/0075* (2013.01); *A61F 2220/0083* (2013.01)

(58) Field of Classification Search
CPC ............ A61F 2/0045; A61F 2220/0075; A61F 2220/0083; A61F 2250/0007; A61F 2250/0021
USPC ................................................ 600/37, 29–32
See application file for complete search history.

(56) References Cited

U.S. PATENT DOCUMENTS

| | | | | |
|---|---|---|---|---|
| 2003/0065402 A1* | 4/2003 | Anderson | A61F 2/0045 | 623/902 |
| 2005/0250977 A1* | 11/2005 | Montpetit | A61F 2/0045 | 600/29 |
| 2006/0089525 A1* | 4/2006 | Mamo | A61B 17/06066 | 600/37 |
| 2009/0221868 A1* | 9/2009 | Evans | A61F 2/0045 | 600/37 |
| 2011/0245589 A1* | 10/2011 | Palma | A61B 17/064 | 600/30 |
| 2015/0374408 A1* | 12/2015 | Ogdahl | A61F 2/0063 | 600/30 |
| 2016/0302904 A1* | 10/2016 | Ogdahl | A61F 2/0045 | |

* cited by examiner

*Primary Examiner* — Sunita Reddy
(74) *Attorney, Agent, or Firm* — Bayramoglu Law Offices LLC

(57) ABSTRACT

An adjustable midurethral sling is provided. The adjustable midurethral sling includes a midurethral sling, a frame, an adjustment suture, a housing, two end parts, tunnel opening hooks, outlets, and tunnel opening hook insertion holes. The adjustable midurethral sling is used in a surgical treatment of an involuntary leakage, wherein the involuntary leakage is defined as a urinary incontinence in cases of an abdominal pressure increase as a result of coughing, sneezing etc.

6 Claims, 10 Drawing Sheets

READJUSTABLE MIDURETHRAL SLING

CROSS REFERENCE TO THE RELATED APPLICATIONS

This application is a divisional (DIV) application of non-provisional application Ser. No. 17/276,497, filed on Mar. 16, 2021, which is the national stage entry of International Application No. PCT/TR2019/050940, filed on Nov. 12, 2019, which is based upon and claims priority to Turkish Patent Application No. 2018/17068, filed on Nov. 13, 2018, and Turkish Patent Application No. 2019/11551, filed on Jul. 31, 2019, the entire contents of which are incorporated herein by reference.

TECHNICAL FIELD

The invention is related to an adjustable midurethral sling used in surgical treatment of involuntary leakage that is defined as stress urinary incontinence occurring in cases of abdominal pressure increase as a result of coughing, sneezing etc.

BACKGROUND

In the prior art, the synthetic mesh that is delivered with carrier needles through the vaginal route, is implanted without a brace from the mid section of the urethra on two parallel (transobturator route) sides or in upwards (retropubic) direction. Separate kits have been defined that are suitable to used from the inside-out and outside-in for the transobturator route and from down-up and up-down usage for the retropubic route during the insertion of the mesh under the urethra. Said insertion process is carried out by rule of thumb according to the nature of this process. When the literature is searched relating to operation techniques, insertion is described in the same way in all cases. However clinical results show that some operations were not efficient due to, loose implantation in some cases and in other cases difficulty during urination was experienced because the implantation was very tight. Although some tests and diagnosis methods have been defined which foresees such results during an evaluation before the operation, the efficacy of such tests have limited value. A valid indication which defines which case requires a looser or a tighter implantation is not available. Therefore the most effectual method is assumed to be the re-adjustment during the short postoperative process after the midurethral sling is inserted, which may be required to be carried out more than once. Various adjustable systems have been defined which allow re-adjustment after operation.

A system similar to said invention is as follows: The mid section of the midurethral sling is made of polypropylene mesh and the side sections have a silicone structure; in the patent this section of the system has been disclosed to be of a structure formed of a (polyester, polypropylene(PP), polyurethane (PU), polyamide (PA), silicon, polytetrafluoroethylene (PTFE), polyethylene terephthalate (PET), latex or thermal shaped plastic) structure. Silicon arms provide an advantage related to easy sliding during the tightening of the mesh. The silicon arms of the mesh may be retropubic or in other words has ends that may face upwards like a U shape or may be transobturator or in other words it may be suitable to be implanted parallel to the ground. The system foreseen for mesh implantation allows implantation from outside to the inside or from down-up. This system allows adjustment such as tightening by pulling from the end sections of the mesh with a minor additional operation after the operation or loosening by pulling from the mid section of the mesh (US 20110245589 A1). In this system a stopper having a plastic structure must be attached to the end section. Any kind of adaptation is not available for the mid section.

Re-operation is required for re-adjustment, although it is not as comprehensive as the actual operation. Moreover even though this system allows a plurality of adjustments, if another adjustment is required the next day after the tightness is adjusted, a new surgical procedure will be required and this constitutes a disadvantage.

SUMMARY

The primary aim of the invention is to allow re-adjustments as much as required, without damaging the mesh according to the incontinence or urination function of the patient during the short phase following midurethral sling operation that is implanted midurethrally.

The sections that are to be used for adjustment of the mesh forming the midurethral sling, have a composite structure which allow easy sliding of the mesh inside the tissue, or in other words they are coated. This coating is biocompatible and as it is only coated on one side it does not lead to an increase in the thickness of the mesh that may prevent healing of the wound. During the pulling and passing of the sutures through the mesh, that are used for adjustment, it is prevented for the mesh to be damaged or ruptured or for its integrity to be disrupted especially due to repeated requirements, by means of the single layer composite structure of the mesh. As the coating is available only on one side, synergy is created by combining the adjustable features due to the easy sliding of the coated surface inside the tissue without losing the advantage of attachment of the mesh arms to the tissue and braceless implantation defined in the action mechanism. The synergy that is created is related to combining the attachment into the tissue and the easy sliding of the coated surface.

By means of the coating the front and back side of the mesh can also be easily distinguished and it is enabled for the right and left side of the mesh to have the same directions. As the adjustment function necessitates that the coated surface faces the front, it is prevented for the mesh to twist around itself or inside the tissue.

The end part does not only ensure that the midurethral sling can be adapted to all applicable directions but it also poses significance in that it overcomes the difficulties of attachment of the mesh to the hook during a surgical operation when said end part is not present. The novelty regarding the end part is not only related to adjustable systems but it is a novelty and invention that can be adapted to all midurethral slings. The sutures are stitched after the mesh is implanted into the tissue, therefore they are provided inside the kit along with the hooks.

BRIEF DESCRIPTION OF THE DRAWINGS

FIG. 3A, Transobturator route in-out and retropubic route down-up implantation feature.

FIG. 3B, Transobturator route out-in and retropubic route up-down implantation feature.

FIG. 4A, View of the coated side of the midurethral sling.

FIG. 4B, View of the uncoated side of the midurethral sling.

REFERENCE NUMBERS

Figure 1:
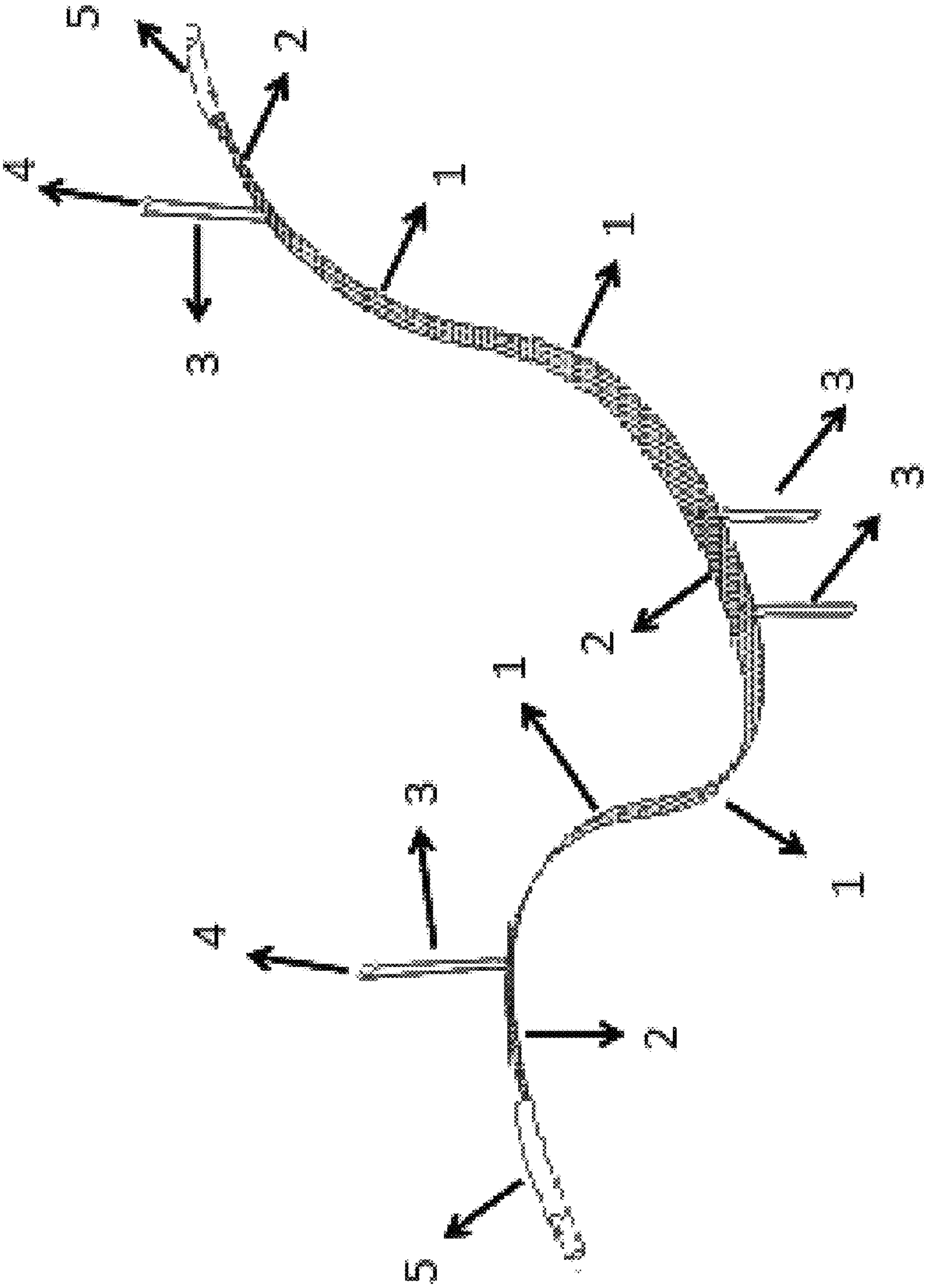
FIG. 1, Adjustable midurethral sling and its attachments.
Figure 2:
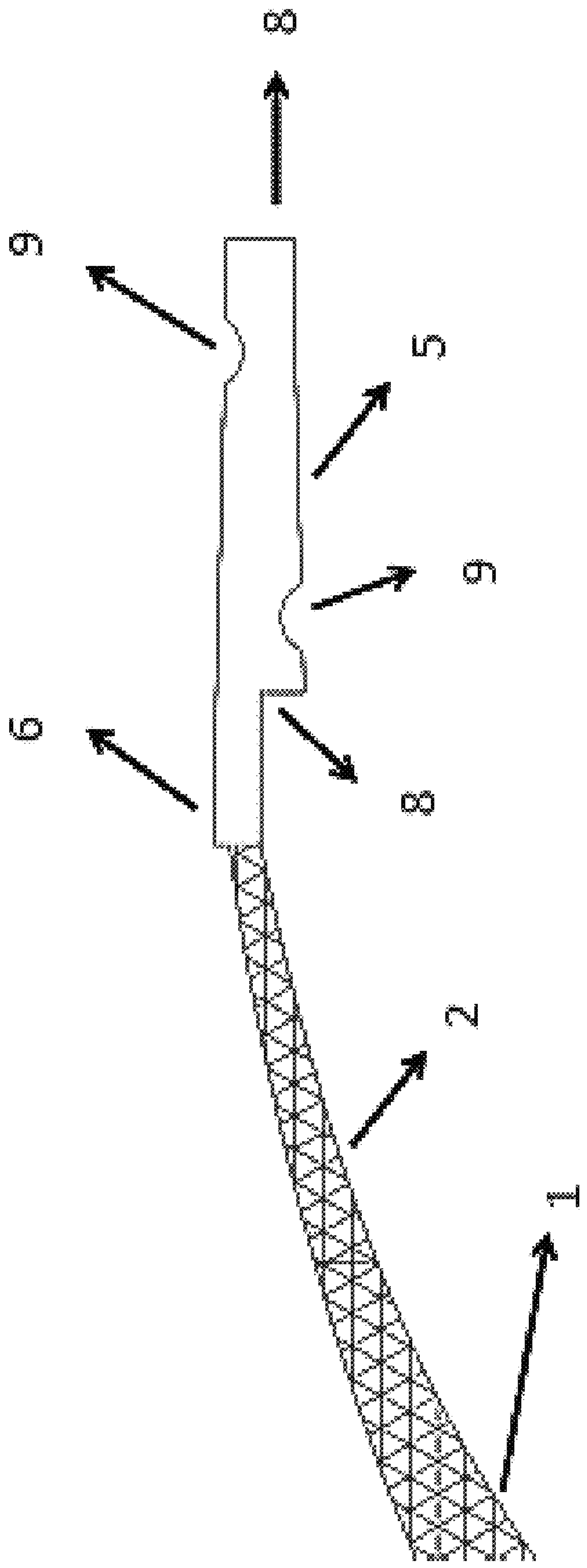
FIG. 2, End parts and midurethral sling articulation of the end part.
Figure 3A:
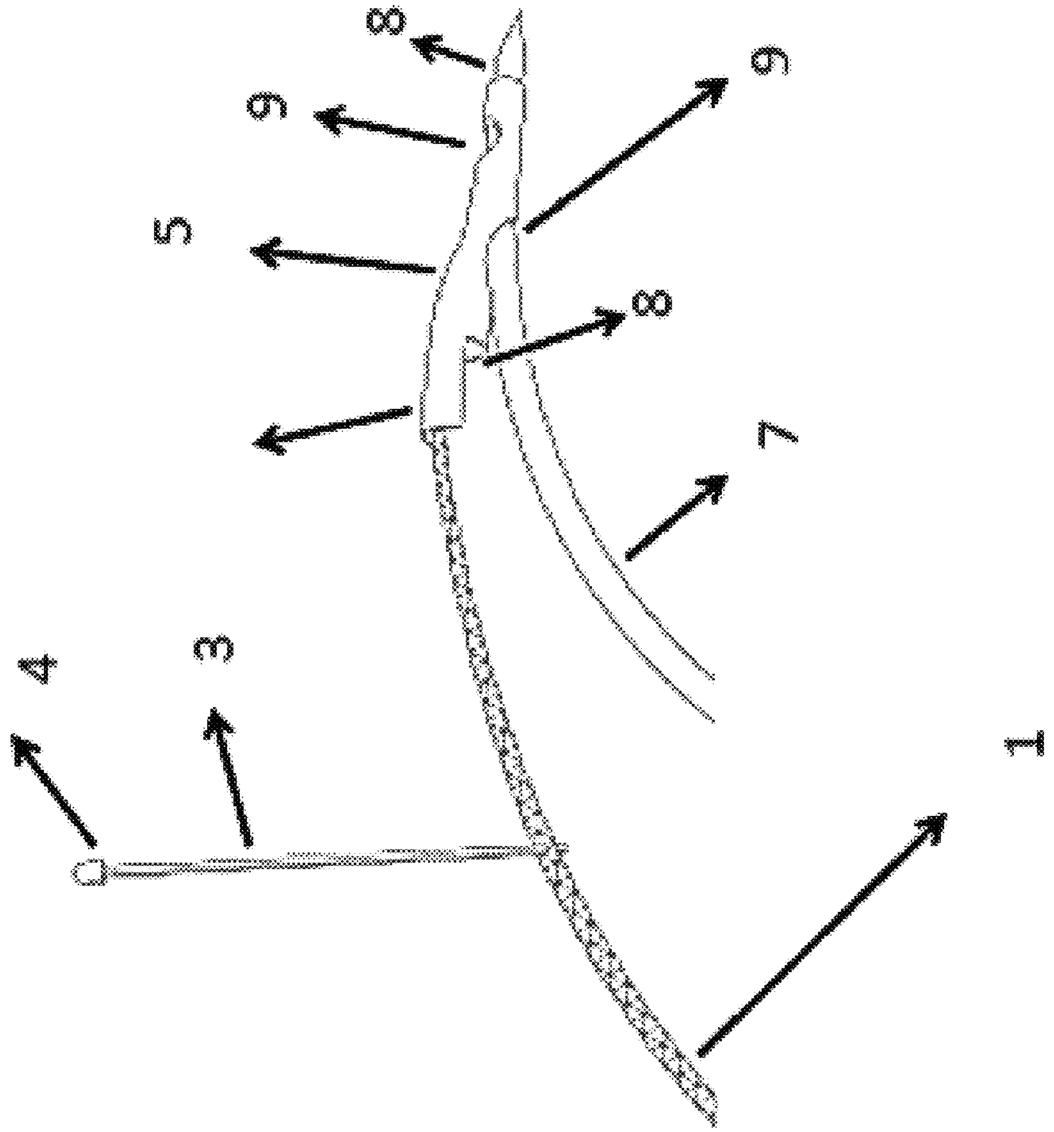
FIGS. 3A and 3B, Hook attachment to the end part enabling tunnel opening from different directions.
Figure 3B:
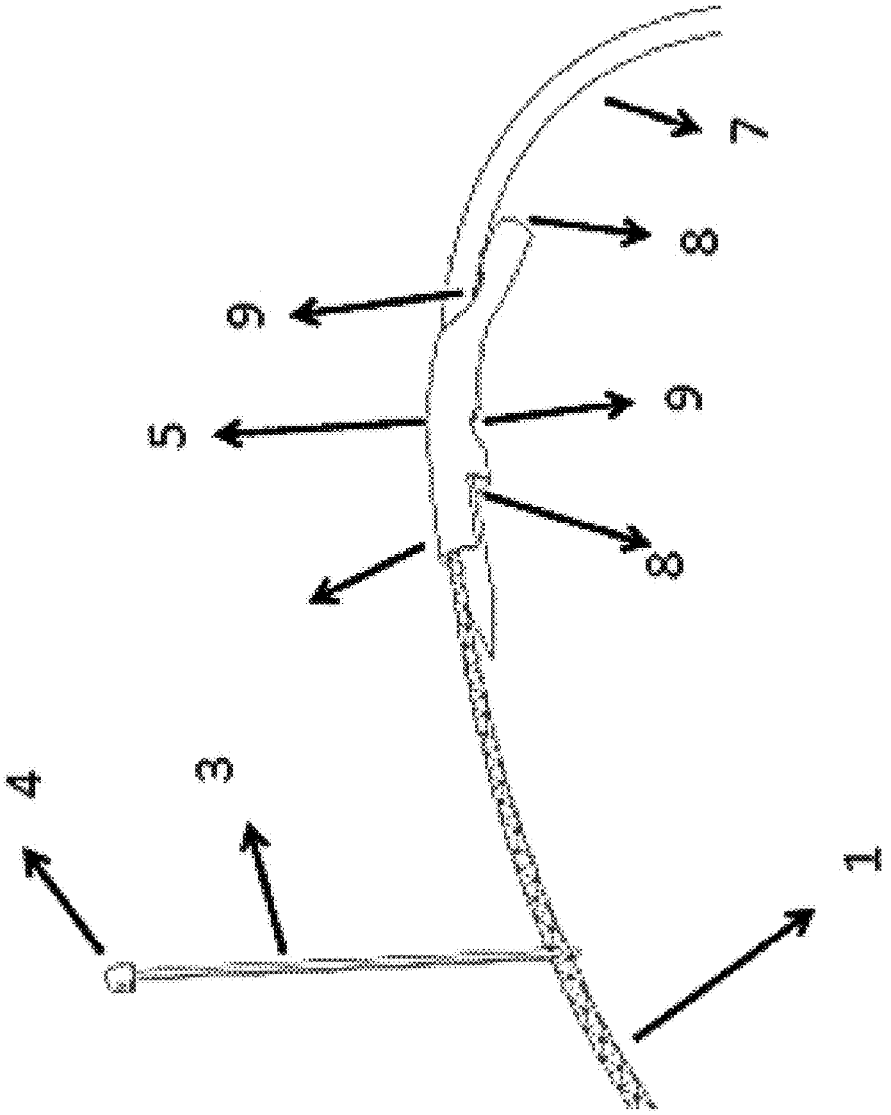
Figure 4A:
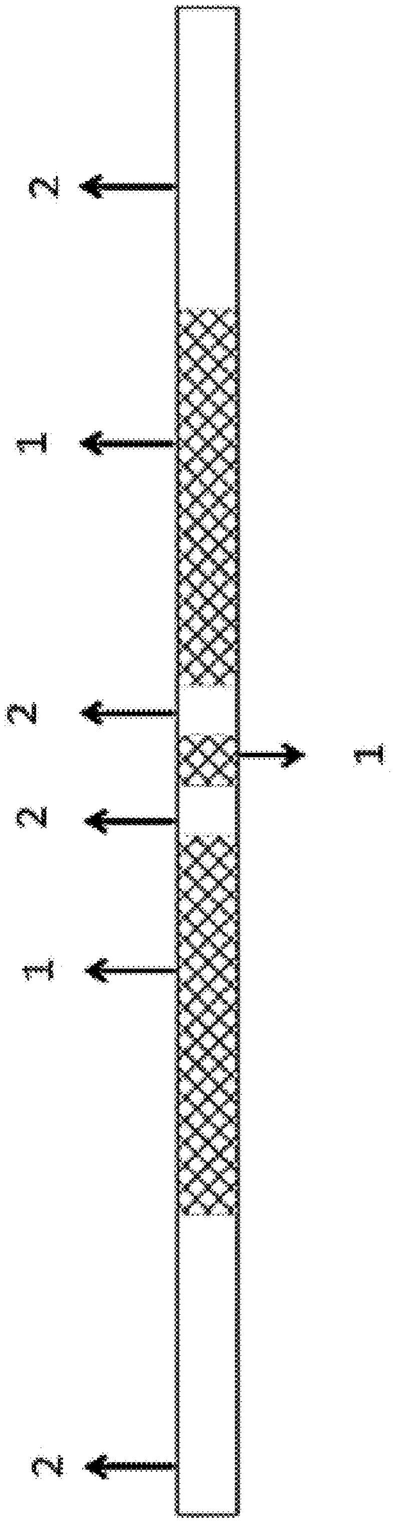
FIGS. 4A and 4B, The views of the coated and uncoated sides of the midurethral sling.
Figure 4B:
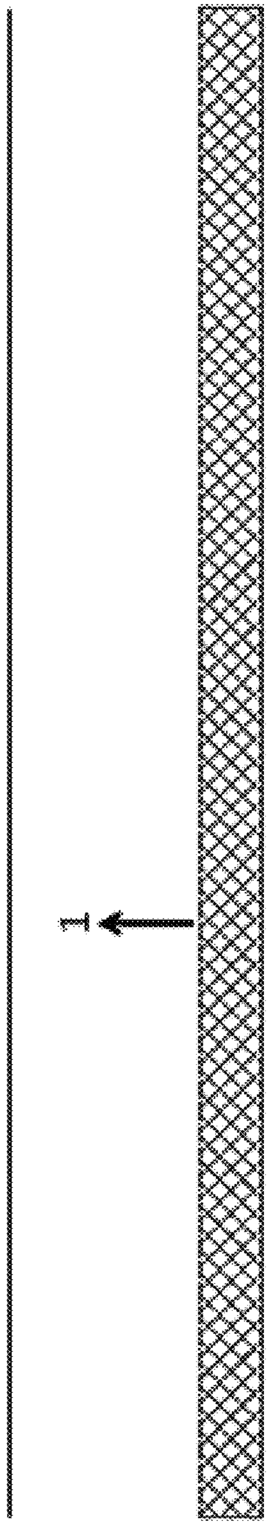
Figure 5:
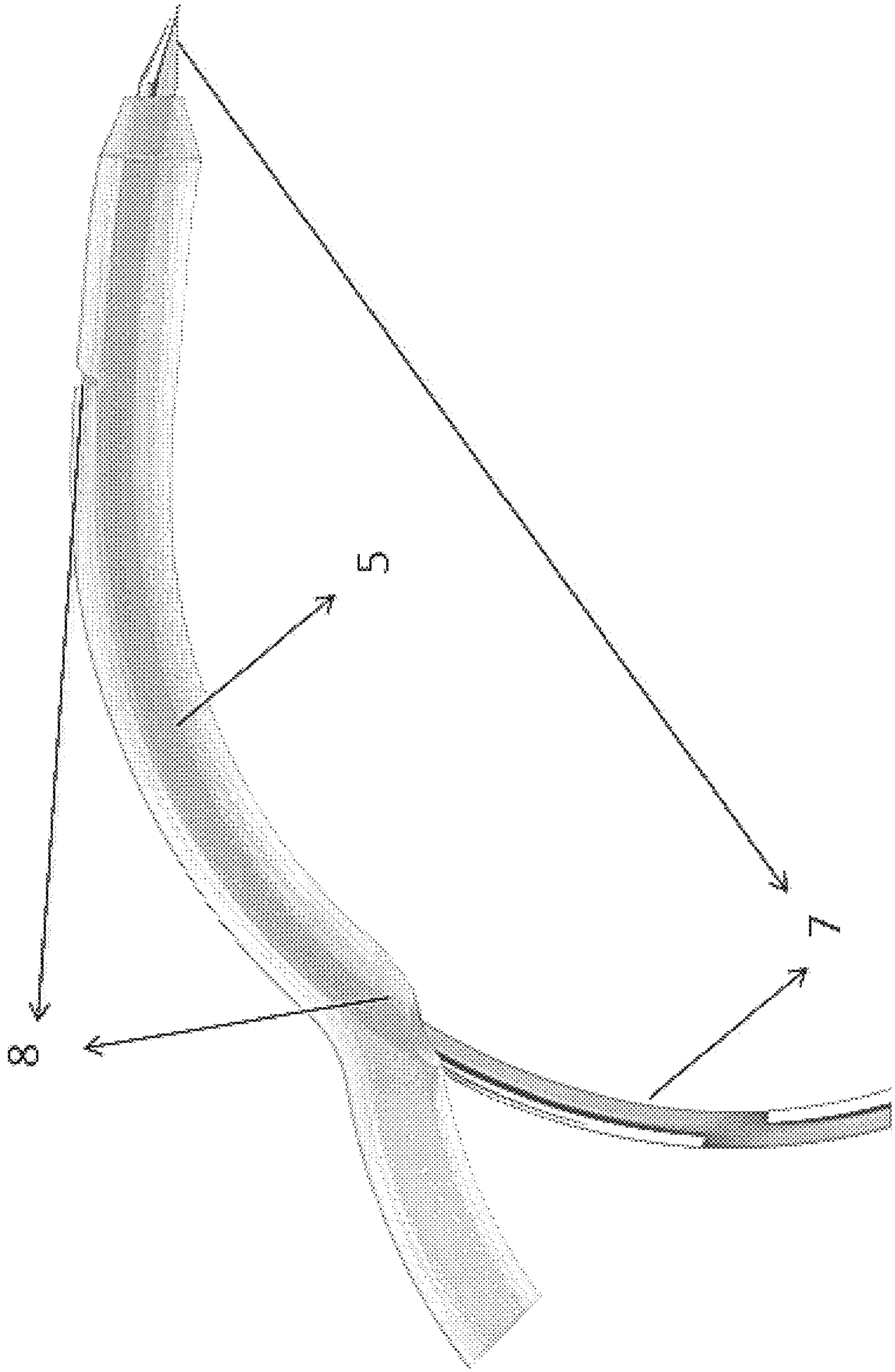
FIG. 5, View of the tunnel opening hook attached to the end part, when the end part is available in the kit in a detached way.
Figure 6:
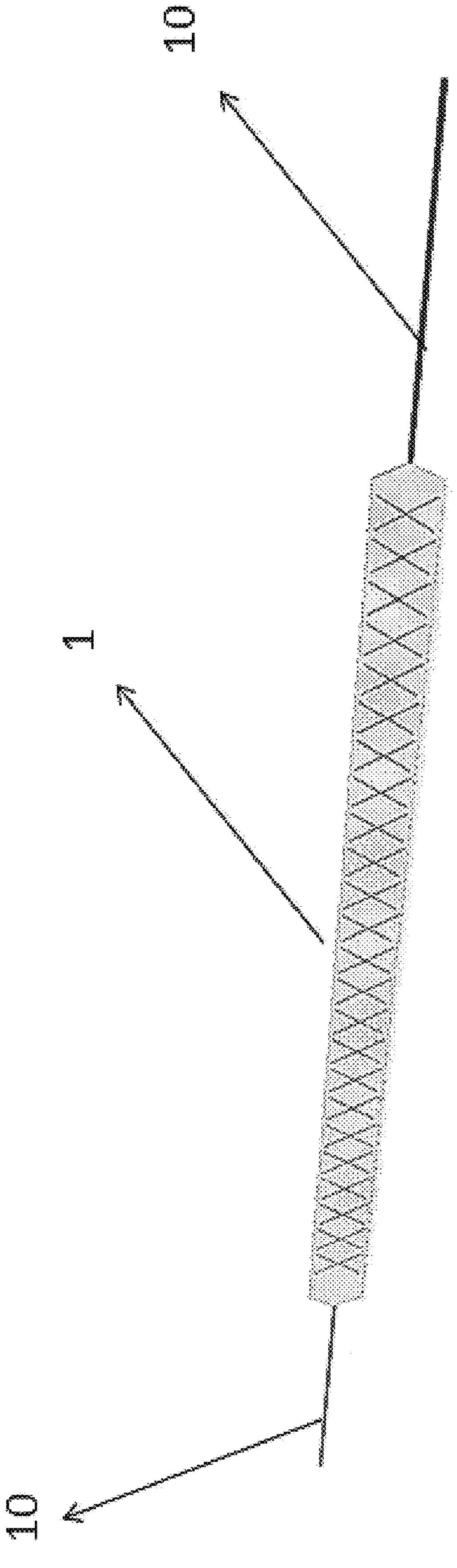
FIG. 6, View of the midurethral sling and the end part guides hinged to said sling which aid in the implantation of the midurethral sling when the end part is available in the kit in a detached way.
Figure 7:
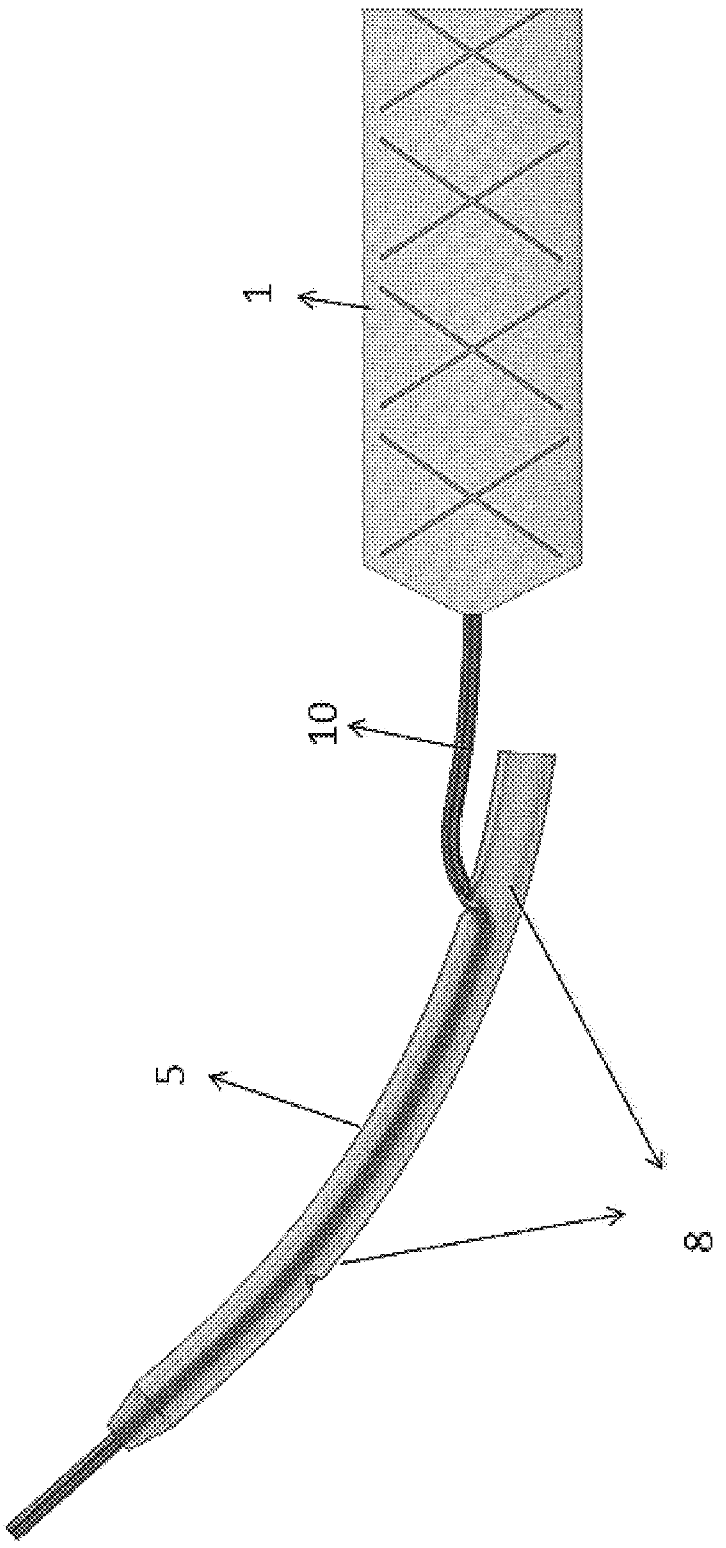
FIG. 7, View of the attachment of the midurethral sling to the end part by means of the end part guides from the transobturator route from outside-inside or from the retropubic route in the down-up direction when the end part is available in the kit in a detached way.
Figure 8:
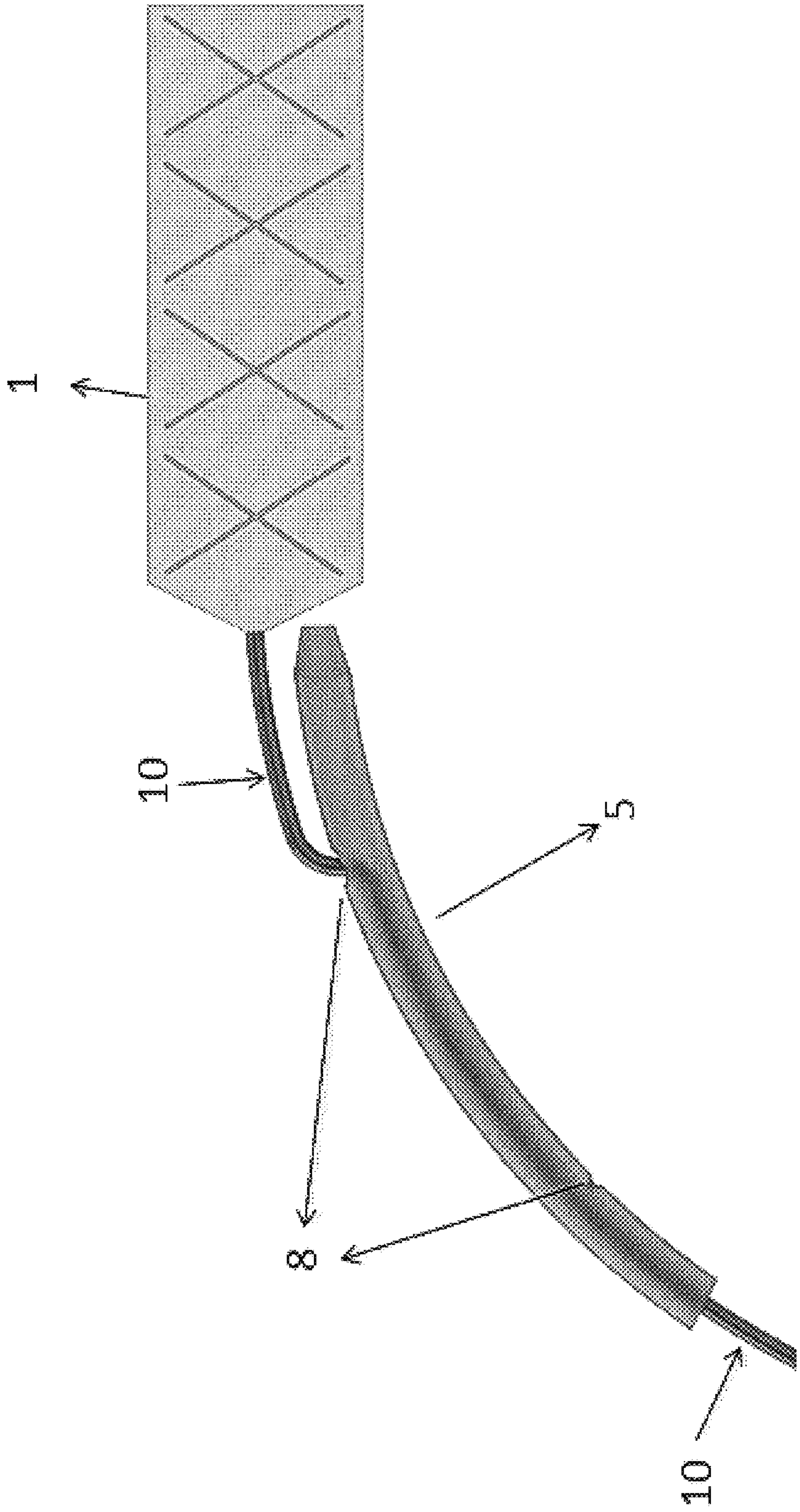
FIG. 8, View of the attachment of the midurethral sling to the end part by means of the end part guides from the transobturator route from inside-outside or from the retropubic route in the up-down direction when the end part is available in the kit in a detached way.

1 Midurethral Sling
2 Single side coating
3 Adjustment suture
4 Adjustment suture housing
5 Midurethral Sling end part
6 Midurethral Sling end part tail section
7 Tunnel opening hook
8 End part outlet holes
9 Tunnel opening hook insertion holes
10 End part guide

DETAILED DESCRIPTION OF THE EMBODIMENTS

A midurethral sling (1) with macro-pores that has been produced from a biocompatible material that has been implanted from the transobturator or retropubic route with a carrier arm to the midurethral region, wherein the mid and side sections thereof comprises sutures which allow the mesh to be readjusted and wherein one side has been covered with a single side coating (2) made of silicon, polyurethane, or polytetrafluoroethylene derivatives such that said coating prevents damaging of the mesh. The material of the midurethral sling (1) can be polyester, polypropylene (PP), polyurethane (PU), polyamide (PA), silicon, polytetrafluoroethylene (PTFE), polyethylene terephthalate (PET), latex or a thermally shaped plastic structure. Having the coating only on one side, ensures that the mesh is not damaged during displacement when the expected technical force is applied, which also allows successive application of the procedure, and besides this the attachment effect of the surface without coating to the desired tissue in order to provide a treatment effect is allowed, therefore a synergy is created where the combination effect is enhanced. In the case that only a mesh is available instead of the coated section, a structure which is not as slippery is obtained; therefore the mesh may be damaged during the re-adjustment procedures in such cases. In the case that the whole mesh is coated the attachment effect to the tissue is weakened. The trauma subjected to the mesh during adjustment is minimized by means of the coating and adjustment is allowed (as many adjustments as necessary) without necessitating the patient to go through a surgical operation even if it is a minor operation. Additionally the usage of an additional material having higher volume or density that is to be attached to the mesh is eliminated by means of the coating process. Biocompatible adhesives can be used in the coating process. These adhesives can be natural or synthetic, collagen based. The single side coating (2) can be provided in the same way at both sides from the exact mid section of the macro-porous midurethral sling that is made of biocompatible material. For tightening, after the mesh is implanted, the suture (3) is passed from the closest coating region remaining under the skin, and is taken out of the side of the incision and is fixed. Therefore a system is provided which allows increasing tightness when both sides are pulled at the same time and which prevents the rupturing of the mesh whilst doing this. In the same way, for the loosening function the two sutures (3) close to the mid section of the mesh are taken out of the side of the vagina case by passing them through the area where coating can be provided, and said sutures are then fixed. Therefore loosening function can be provided if necessary. The needles that are provided at the end sections of the sutures designed for providing the adjustment function are cut after being taken outside, and are knotted to each other or if they are not knotted they can be placed inside a housing (4). When the function related to adjustment is completed the sutures are cut and removed easily. The midurethral sling (1) has been attached from the tail section (6) at both sides to the end part (5), that is made of a biocompatible high density polyethylene, silicon, natural rubber, soft PVC and other similar material. The end part (5) is such that it is biocompatible and it can tightly grip the metal tunnel opening hook (7). The end part (5) must allow the usage of the tunnel opening hook (7) according to the implantation route of the midurethral sling, namely from the transobturator route, in-out, out-in, or retropubic route as down-up, up-down. When the end part (5) is attached to the tunnel opening hook (7), it is attached such that it tightly winds around the hook in order to ensure that the midurethral sling (1) does not detach itself from the hook against the resilience it shall encounter when travelling through the tissue. The end parts (5) can not only be fixed to the midurethral sling (1) but they can also be provided as detached parts inside the set. In such a case the end part (5) shall be placed according to the desired direction, independent from the tunnel opening hook and the midurethral sling (1). Following this, when the tunnel opening hook (7) is taken out, an end part (5) which is ready to implant the midurethral sling (1) can be obtained inside the tunnel. At this stage, the midurethral sling (1) shall be able to be implanted into the body by being driven, using the tunnel opening hook attachment holes (9) from inside the end part (5) via the end part guides (10) located at the ends thereof. When the midurethral sling (1) is implanted into the body, the end part (5) and the end part guides (10) are removed and the procedure is completed. In the case that the end part (5) is fixedly attached to the midurethral sling (1), the transobturator application shall be as in-out or out-in. This situation is suitable only for the usage of the dominant hand of the expert carrying out the application in one direction. In the case that the end part (5) is provided as an independent part inside the kit, and the midurethral sling (1) is implanted into the body by being passed through the end part (5) via the end part guides (10), the person carrying out the application can use his/her dominant hand in both directions. When the end part (5) is provided as an independent part inside the kit, this allows the synchronous moving of the midurethral sling (1) via the end part guides (10) in both directions.

There may be three types of hooks inside the set; one each for two types, two for another type that is left and right; the total of the hooks can be 5 at most. The novelty is that the desired hook can be used for all application types, without needing to make any changes on the mesh. In order for the end part (5) to be able to be attached via the hook at the desired frequency to all routes mentioned above, the outlets (8) on both ends of the end part are smaller in dimension when compared to the body; and at the top and the bottom proximal to the outlets (8) entrance holes (9) into which the tunnel opening hook (7) is inserted to the end part (5), are provided. After the midurethral sling (1) is implanted, first the tunnel opening hooks (7) and then the end parts (6) are removed from the area of implantation. Following this a suture (3) is stitched to the midurethral sling (1) under the skin at a section that is closest to said sling and afterwards the suture is taken out of the incision area and is kept inside a housing (4) outside the skin. The same procedure shall be carried out from the mid section of the vagina wall and this loosening function is provided. When the end parts (5) are provided independently inside the kit and the end part guides (10) are used for midurethral sling implantation (1), the independent end parts (5) are placed via the tunnel opening hooks (7) inside the body at the desired direction and the guides (10) are removed from the tunnel opening hooks (7) leaving the midurethral sling inside the tunnel that has been prepared. The midurethral sling (1) is moved by means of the hook attachment holes (9) from inside the end parts (5) via the end part guides (10). When the end part guide (10) is visible outside the tissue after being moved inside the end part (5), first of all the end part (5) is removed and then the end part guide (10) is separated outside of the skin, from the midurethral sling (1). The implantation and adjustment applications following this, is the same with the applications where the end part (5) is fixed to the midurethral sling (1).

What is claimed is:

1. A re-adjustable midurethral sling assembly, comprising:

a midurethral sling, wherein the midurethral sling is implanted from a transobturator or retropubic route to a midurethral region, an adjustment suture coupled to the midurethral sling and is configured for re-adjusting the midurethral sling, two detachable end parts each attached to an end of the midurethral sling, a tunnel opening hook configured to be attached to a respective end part of one of the two detachable end parts at an application direction in a surgery, outlets, wherein the outlets are respectively provided at each end part of the two detachable end parts, and are configured to attach each end part of the two detachable end parts tightly to the tunnel opening hook, and an end part guide passing through an end part of the two detachable end parts;

wherein the outlets provide different configurations for the end parts guide to pass through the end part of the two detachable end parts; and wherein the two detachable end parts, the tunnel opening hook, and the end part guide are configured to be removed after the midurethral sling is left implanted in a desired position.

2. The re-adjustable midurethral sling assembly according to claim 1, wherein the midurethral sling is macroporous.

3. The re-adjustable midurethral sling assembly according to claim 1, wherein material of the midurethral sling is selected from the group consisting of polyester, polypropylene, polyurethane, polyamide, silicon, polytetrafluoroethylene, polyethylene terephthalate, a latex and a thermally shaped plastic.

4. The re-adjustable midurethral sling assembly according to claim 1, wherein material of a coating is selected from the group consisting of polyester, polypropylene, polyurethane, polyamide, silicon, polytetrafluoroethylene, polyethylene-terephthalate, a biopolymer, a latex and a thermally hardened plastic.

5. The re-adjustable midurethral sling assembly according to claim 1, wherein material of the each end part of the two detachable end parts is selected from the group consisting of polyethylene, silicon rubber, natural rubber, soft polyvinyl, a thermally shaped biocompatible plastic and an elastic biopolymer.

6. The re-adjustable midurethral sling assembly according to claim 1, wherein the tunnel opening hook is biocompatible.

* * * * *